US009517261B2

(12) United States Patent
Feederle et al.

(10) Patent No.: US 9,517,261 B2
(45) Date of Patent: Dec. 13, 2016

(54) SECOND GENERATION VIRUS-LIKE PARTICLES (VLP) FROM EPSTEIN-BARR VIRUSES FOR VACCINATION PURPOSES

(71) Applicant: Deutsches Krebsforschungszentrum, Heidelberg (DE)

(72) Inventors: Regina Feederle, Heidelberg (DE); Sophia Hundt, Heidelberg (DE); Henri-Jacques Delecluse, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 31 days.

(21) Appl. No.: 14/366,645

(22) PCT Filed: Dec. 28, 2012

(86) PCT No.: PCT/EP2012/077007
§ 371 (c)(1),
(2) Date: Jun. 18, 2014

(87) PCT Pub. No.: WO2013/098364
PCT Pub. Date: Jul. 4, 2013

(65) Prior Publication Data
US 2014/0322255 A1 Oct. 30, 2014

(30) Foreign Application Priority Data

Dec. 30, 2011 (EP) .................................... 11196215

(51) Int. Cl.
*A61K 39/245* (2006.01)
*C12N 15/86* (2006.01)
*C12N 7/00* (2006.01)
*A61K 39/00* (2006.01)
*A61K 39/12* (2006.01)
*C07K 14/005* (2006.01)
*C07K 16/08* (2006.01)

(52) U.S. Cl.
CPC ............. *A61K 39/245* (2013.01); *A61K 39/12* (2013.01); *C12N 7/00* (2013.01); *C12N 15/86* (2013.01); *A61K 2039/5258* (2013.01); *C12N 2710/16223* (2013.01); *C12N 2710/16234* (2013.01); *C12N 2710/16242* (2013.01); *C12N 2710/16243* (2013.01); *C12N 2710/16262* (2013.01); *C12N 2800/204* (2013.01)

(58) Field of Classification Search
CPC .................. A61K 39/245; A61K 39/12; A61K 2039/5258; C12N 15/86; C12N 7/00; C12N 2710/16234; C12N 2800/204; C12N 2710/16243; C12N 2710/16242; C12N 2710/16223; C12N 2710/16262; C12N 2710/00041; C12N 2710/16134; C12N 2710/16171; C12N 2710/16634; C12N 2710/20034; C12N 2700/00; C12N 2710/10021; C12N 2710/16734; C07K 14/005; C07K 16/081; C07K 14/05
See application file for complete search history.

(56) References Cited

U.S. PATENT DOCUMENTS

| 9,028,840 B2 * | 5/2015 | Adhikary et al. ......... 424/230.1 |
| 2004/0009469 A1 * | 1/2004 | Apt et al. .................... 435/5 |
| 2007/0087331 A1 * | 4/2007 | Bachmann et al. ............ 435/5 |
| 2008/0044437 A1 * | 2/2008 | Chen ......................... 424/204.1 |
| 2010/0150961 A1 * | 6/2010 | Vedvick ................... C12N 7/00 424/216.1 |
| 2012/0301494 A1 * | 11/2012 | Cheng .................... A61K 39/21 424/189.1 |

FOREIGN PATENT DOCUMENTS

| CA | WO 2010047839 A1 * | 4/2010 | ........... C07K 14/005 |
| EP | 2 065 462 A1 | 6/2009 | |

OTHER PUBLICATIONS

Hellebrand E, Mautner J, Reisbach G, Nimmerjahn F, Hallek M, Mocikat R, Hammerschmidt W. Epstein-Barr virus vector-mediated gene transfer into human B cells: potential for antitumor vaccination. Gene Ther. Jan. 2006;13(2):150-62.*
Farina A, Feederle R, Raffa S, Gonnella R, Santarelli R, Frati L, Angeloni A, Torrisi MR, Faggioni A, Delecluse HJ. BFRF1 of Epstein-Barr virus is essential for efficient primary viral envelopment and egress. J Virol. Mar. 2005;79(6):3703-12.*
Kieff and B. Rickinson. (2006), Epstein-Barr virus and its replication, In D. M. Knipe and P. M. Howley (ed.), Fields virology, 5th ed. Lippincott-Raven, Philadelphia, PA. 2603-2654.
de Jesus O et al., "Updated Epstein-Barr virus (EBV) DNA sequence and analysis of a promoter for the BART (CST, BARFO) RNAs of EBV," (2003) J. Gen. Virol. 84, 1443-1450.
Dolan A et al., "The Genome of Epstein-Barr Virus Type 2 Strain AG876," (2006) Virology vol. 350, 164-170.
Feederle, R, et al. (2006), Epstein-Barr virus BNRF1 protein allows efficient transfer from the endosomal compartment to the nucleus of primary B lymphocytes. J Virol. 80(19):9435-43.
Hammerschmidt W, Sudgen B (1989) Genetic analysis of immortalizing functions of Epstein-Barr virus in human B-lymphocytes. Nature 340: 393-397.

(Continued)

*Primary Examiner* — Rachel B Gill
(74) *Attorney, Agent, or Firm* — Foley & Lardner LLP

(57) ABSTRACT

The present invention relates to an Epstein-Barr virus-like particle (EB-VLP) substantially free of Epstein-Barr Virus (EBV) DNA. The present invention also relates to a polynucleotide comprising an EBV genome a) lacking at least one expressible gene selected from the group consisting of the BFLF1 gene, the BBRF gene, the BGRF1 gene, the BDRF1 gene, the BALF3 gene, the BFRF1A gene, and the BFRF1 gene, and b) producing the EB-VLP of the invention in a suitable host cell. The present invention further relates to a vector and a host cell comprising the polynucleotide of the invention as well to a method of manufacturing the EB-VLPs, a method of manufacturing a vaccine thereof, a vaccine and a composition comprising the EB-VLPs.

17 Claims, 9 Drawing Sheets

(56) References Cited

OTHER PUBLICATIONS

Figure 1:
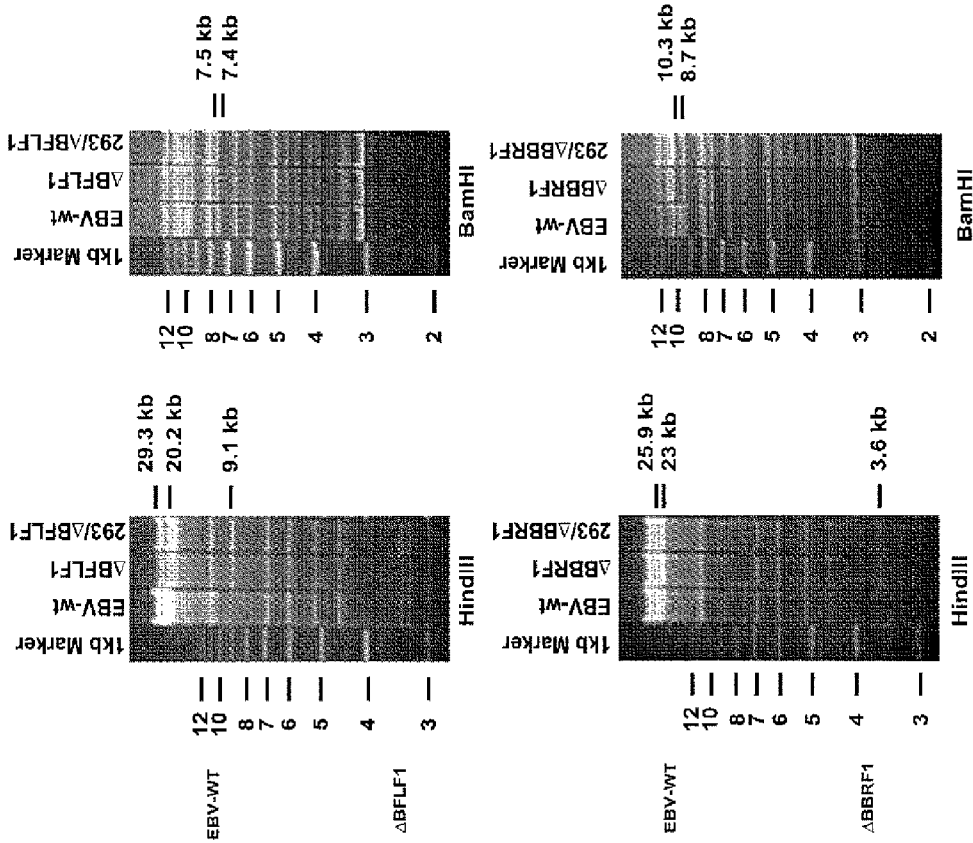
Figure 1:
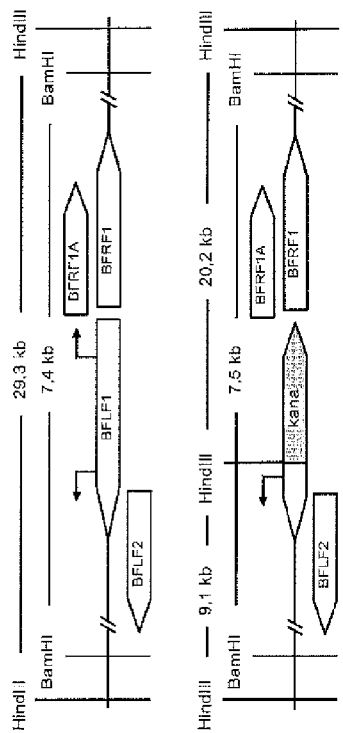
Figure 1:
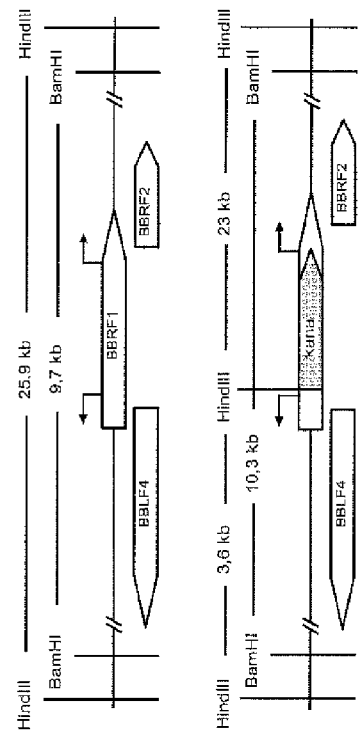

Cohen JI, et al. (1989) Epstein-Barr virus nuclear protein 2 is a key determinant of lymphocyte transformation. PNAS 86:9558-9562.
Kaye KM, et al. (1993) Epstein-Barr virus latent membrane protein 1 is essential for B-lymphocyte growth transformation. PNAS, 90, 9150-9154.
Tomkinson B, et al. (1993) Epstein-Barr virus nuclear proteins EBNA3A and EBNA3C are essential for B-lymphocyte growth transformation. J. Virol. 62:6762-6771.
Delecluse et al., "Propagation and recovery of intact, infectious Epstein-Barr virus from prokaryotic to human cells," Proc Natl Acad Sci U S A. Jul. 7, 1998;95(14):8245-50.
Delecluse, et al., "A first-generation packaging cell line for Epstein-Barr virus-derived vectors," Natl Acad Sci U S A. Apr. 27, 1999;96(9):5188-93.
Küppers, R. (2003). B cells under influence: transformation of B cells by Epstein-Barr virus, Nat. Rev. Immunol. 3:801-812.
Laichalk, L. L., and D. A. Thorley-Lawson. (2005), Terminal differentiation into plasma cells initiates the replicative cycle of Epstein-Barr virus in vivo. J. Virol. 79:1296-1307.
Rickinson, A. B., and E. Kieff. (2006), Epstein-Barr virus, In D. M. Knipe and P. M. Howley (ed.), Fields virology, 5th ed. Lippincott-Raven, Philadelphia, PA., 2655-2700.
Rooney, C. M., et al., (1998), Infusion of cytotoxic T cells for the prevention and treatment of Epstein-Barr virus-induced lymphoma in allogeneic transplant recipients. Blood 92:1549-1555.
Rees L, et al. (2009), A phase I trial of Epstein-Barr virus gp350 vaccine for children with chronic kidney disease awaiting transplantation. Transplantation 88(8):1025-9.
Greenstone, H. L., et. al. (1998), Chimeric papillomavirus virus-like particles elicit antitumor immunity against the E7 oncoprotein in an HPV16 tumor model. Proc. Natl. Acad. Sci. USA 95:1800-1805.
Mandic, A., and T. Vujkov. (2004). Human papillomavirus vaccine as a new way of preventing cervical cancer: a dream or the future? Ann. Oncol. 15:197-200.
Roizman, B., and D. M. Knipe. (2001), Herpes simplex viruses and their replication, In D. M. Knipe, P. M. Howley, D. E. Griffin, R. A. Lamb, M. A. Martin, B. Roizman, and S. E. Straus (ed.), Fields virology, 4th ed., vol. 2. Lippincott Williams & Wilkins, Philadelphia, Pa., 2399-2459.
Feederle R, et al., (2005), Defective infectious particles and rare packaged genomes produced by cells carrying terminal-repeat-negative Epstein-Barr virus. J. Virol. 79; 7641-7.
Ruiss Romana et al: "A virus-like particle-based Epstein-Barr virus vaccine.", Journal of Virology Dec. 2011, vol. 85, No. 24, Oct. 12, 2011, pp. 13105-13113.
Granato Marisa et al: "Deletion of Epstein-Barr virus BFLF2 leads to impaired viral DNA packaging and primary egress as well as to the production of defective viral particles", Journal of Virology, The American Society for Microbiology, US, vol. 82, No. 8, Apr. 1, 2008, pp. 4042-4051.
Feederle et al., "Epstein-Barr Virus Genetics: Talking about the BAC Generation," *Herpesviridae* Biomed Central LTD, vol. 1, No. 6, (2010), 13 pages.
Hettich E et al: "Genetic design of an optimized packaging cell line for gene vectors transducing human B cells", Gene Therapy, Macmillan Press Ltd., Basingstoke, GB, vol. 13, No. 10, May 1, 2006, pp. 844-856.
Farina Antonella et al: "BFRF1 of Epstein-Barr virus is essential for efficient primary viral envelopment and egress.", Journal of Virology Mar. 2005, vol. 79, No. 6, pp. 3703-3712.
Pavlova Sophia et al: "An Epstein-barr virus mutant produces immunogenic defective particles devoid of viral DNA.", Journal of Virology Feb. 2013, vol. 87, No. 4, Dec. 12, 2012, pp. 2011-2022.
International Search Report issued in related International Patent Application No. PCT/EP2012/077007, mailed Feb. 28, 2013.
International Preliminary Report on Patentability issued in related International Patent Application No. PCT/EP2012/077007, issued Jul. 1, 2014.
Gonnella et al., "Characterization and Intracellular Localization of the Epstein-Barr Virus Protein BFLF2: Interactions with BFRF1 and with the Nuclear Lamina," *Journal of Virology*, pp. 3713-3727 (2005).
Yu et al., "Genetic Analysis of the UL 15 Gene Locus for the Putative Terminase of Herpes Simplex Virus Type 1," *Virology*, vol. 243, pp. 32-44 (1998).
Beard et al., "DNA Cleavage and Packaging Proteins Encoded by Genes UI28, UI15, and UL33 of Herpes Simplex Virus Type 1 Form a Complex in Infected Cells," *Journal. of Virology*, pp. 4785-4791 (2002).

\* cited by examiner

WT

ΔBFLF1

RPMI

ΔTR

SECOND GENERATION VIRUS-LIKE PARTICLES (VLP) FROM EPSTEIN-BARR VIRUSES FOR VACCINATION PURPOSES

The present invention relates to an Epstein-Barr virus-like particle (EB-VLP) substantially free of Epstein-Barr Virus (EBV) DNA. The present invention also relates to a polynucleotide comprising an EBV genome a) lacking at least one expressible gene selected from the group consisting of the BFLF1 gene, the BBRF1 gene, the BGRF1 gene, the BDRF1 gene, the BALF3 gene, the BFRF1A gene, and the BFRF1 gene, and b) producing the EB-VLP of the invention in a suitable host cell. The present invention further relates to a vector and a host cell comprising the polynucleotide of the invention as well as to a method of manufacturing said EB-VLPs, a method of manufacturing a vaccine thereof, a vaccine and a composition comprising said EB-VLPs.

The oncogenic Epstein-Barr virus (EBV) belongs to the family of gammaherpesviruses that can infect human B lymphocytes latently. The EBV establishes lifelong persistent B-cell infections in more than 90% of the human population (Kieff and B. Rickinson. (2006), Epstein-Barr virus and its replication, In D. M. Knipe and P. M. Howley (ed.), Fields virology, 5th ed. Lippincott-Raven, Philadelphia, Pa. 2603-2654; Küppers, R. (2003). B cells under influence: transformation of B cells by Epstein-Barr virus, Nat. Rev. Immunol. 3:801-812). In healthy individuals, the majority of EBV infected B cells show limited viral gene expression and a resting phenotype. The terminal differentiation of latently infected cells into plasma cells leads to virus reactivation, production, and reinfection of B cells (Laichalk, L. L., and D. A. Thorley-Lawson. (2005), Terminal differentiation into plasma cells initiates the replicative cycle of Epstein-Barr virus in vivo. J. Virol. 79:1296-1307). The expression of all viral latency genes causes growth transformation and the proliferation of infected B cells, which is reflected by the outgrowth of EBV-transformed lymphoblastoid B-cell lines in vitro and by the association of EBV with a variety of B-cell lymphoproliferative diseases, including different types of lymphoma, in vivo. EBV infection is controlled by T cells, as indicated by an increased incidence of EBV-associated malignancies in patients with congenital or iatrogenically induced T-cell dysfunction (Rickinson, A. B., and E. Kieff. (2006), Epstein-Barr virus, In D. M. Knipe and P. M. Howley (ed.), Fields virology, 5th ed. Lippincott-Raven, Philadelphia, Pa., 2655-2700.) and by the successful treatment of EBV-associated posttransplant lymphoproliferative disease in hematopoietic stem cell transplant recipients by the infusion of polyclonal EBV-specific T-cell lines (Rooney, C. M., et al., (1998), Infusion of cytotoxic T cells for the prevention and treatment of Epstein-Barr virus-induced lymphoma in allogeneic transplant recipients. Blood 92:1549-1555).

There is thus a need in the art to develop a vaccine to prevent or clear EBV infection. Such a vaccine would be applied to an apparently healthy subject, so safety of such a vaccine would be a major concern. So far, there is only a peptidic vaccine against EBV gp350 commercially available. However, first clinical trials with this vaccine show it does not prevent EBV infection in EBV-negative transplant recipients (Rees L, et al. (2009), A phase I trial of Epstein-Barr virus gp350 vaccine for children with chronic kidney disease awaiting transplantation. Transplantation 88(8): 1025-9.).

Virus-like particles (VLPs) are structures similar or identical to mature virions but lack the viral genome. In general, they stimulate the host's immune response to a higher extent than e.g. monomeric peptides do, which is why they have been preferentially used for vaccination against several viruses such as hepatitis B and papillomavirus (Greenstone, H. L., et. al. (1998), Chimeric papillomavirus virus-like particles elicit antitumor immunity against the E7 oncoprotein in an HPV16 tumor model. Proc. Natl. Acad. Sci. USA 95:1800-1805; Mandic, A., and T. Vujkov. (2004). Human papillomavirus vaccine as a new way of preventing cervical cancer: a dream or the future? Ann. Oncol. 15:197-200). A crucial safety aspect of VLP vaccine regimes is that the VLPs used have to be free of viral genomes (DNA or RNA), since otherwise vaccination could induce virus replication and/or latent infection by the virus.

The viral lytic replication, i.e. the processes leading to the formation of progeny viral particles, of EBV and other herpesviruses is a complex process that results from sequential activation of different protein classes. During lytic replication, the viral genome is amplified several thousand times from the different origins of replication to form highly branched structures. These large concatemers are then resolved into unit-length linear viral genomes that will be packaged into preformed procapsids within the infected cell nucleus. Capsids containing viral DNA will undergo further conformational and structural changes and egress from the infected cell as enveloped virion particles (Roizman, B., and D. M. Knipe. (2001), Herpes simplex viruses and their replication, In D. M. Knipe, P. M. Howley, D. E. Griffin, R. A. Lamb, M. A. Martin, B. Roizman, and S. E. Straus (ed.), Fields virology, 4th ed., vol. 2. Lippincott Williams & Wilkins, Philadelphia, Pa., 2399-2459.). One essential cis element that leads to EBV encapsidation are the terminal repeats (TRs) located at both ends of the linear genome that are involved in the excision of individual viral genomes from the concatemers formed during viral lytic replication as well as in their packaging. An EBV mutant strain in which these terminal repeats had been deleted (delTR-EBV) has been generated. It has been shown that after induction of the lytic cycle a large amount of empty EB-VLPs is produced and that the efficiency of genome encapsidation is markedly low, since as few as 0.001% of cells infected with supernatants containing delTR-EBV express a marker gene from said genome, as compared to 29% when a control EBV is used (Feederle R, et al., (2005), Defective infectious particles and rare packaged genomes produced by cells carrying terminal-repeat-negative Epstein-Barr virus. J. Virol. 79; 7641-7) This indicates that the terminal repeats are important but not absolutely essential for genome encapsidation. Moreover, it has been shown that VLPs produced from delTR-EBV still—though rarely—infect cells, thus not warranting safety of the delTR-EBV VLPs for use as a vaccine.

In summary, notwithstanding the existing need, so far no method for producing a safe and efficient vaccine against EBV has been developed. Thus, the technical problem underlying the invention can be seen as the provision of means and methods which allow for the efficient production of an EBV vaccine. The technical problem is solved by the embodiments characterized in the claims and herein below.

Therefore the present invention relates to an Epstein-Barr virus-like particle (EB-VLP) substantially free of Epstein-Barr Virus (EBV) DNA.

The term "Epstein-Barr virus like particle" or "EB-VLP" as used herein refers to a viral particle derived from an EBV neither replicating lytically nor establishing latent infection in a suitable host cell. EB-VLPs, preferably, have an essentially typical herpesviral structure as analysed by electron microscopy, i.e. they have a capsid, a tegument, and an outer membrane. However, in contrast to the normal herpesviral particle, the EB-VLPs of the present invention are empty, i.e. they do not contain EBV DNA, preferably no DNA at all. The EB-VLPs comprise the EB-viral proteins (e.g., capsid, tegument, coat, shell, surface or envelope proteins and glycoproteins) known to the skilled artisan for the known EBV types (e.g. EBV type 1: Genbank Acc No: NC_007605.1 GI:82503188; genome: SEQ ID NO: 1; de Jesus O et al. (2003) J. Gen. Virol. 84, 1443-1450 and EBV type 2: Genbank Acc No: NC_009334.1 GI:139424470; Dolan A et al. (2006) Virology Vol. 350, 164-170), genome: SEQ ID NO: 2, including strain M81 (SEQ ID NO: 38)).

In addition to EBV-encoded proteins, the EB-VLP may also comprise one or more artificial polypeptides. The term "artificial polypeptide" relates to any polypeptide incorporated into an EB-VLP which is not comprised in a wildtype EBV. If an artificial polypeptide is incorporated into, and therefore comprised in, an EB-VLP, can be assessed by obtaining EB-VLPs according to the methods of the present invention, separating EB-VLPs from the producing cells, e.g. by centrifugation or by immunoprecipitation as described in the examples below, followed by determining the presence of the artificial polypeptide in said EB-VLPs, which can be accomplished e.g. by the immunoblot method described in the examples or by any other method suited for the specific polypeptide and known to the artisan.

Preferably, the artificial polypeptide is a fusion polypeptide comprising a membrane-integral part of a herpesviral glycoprotein. More preferably, the artificial polypeptide is a fusion polypeptide comprising the transmembrane domain of the herpes simplex virus gC protein.

In a preferred embodiment the artificial polypeptide further comprises a detectable tag. The term "detectable tag" refers to a stretch of amino acids which are added to or introduced into the fusion polypeptide of the invention. Preferably, the tag shall be added C- or N-terminally to the fusion polypeptide of the present invention. The said stretch of amino acids shall allow for detection of the fusion polypeptide by an antibody which specifically recognizes the tag or it shall allow for forming a functional conformation, such as a chelator or it shall allow for visualization by fluorescent tags. Preferred tags are the Myc-tag, FLAG-tag, 6-His-tag, HA-tag, GST-tag or GFP-tag. These tags are all well known in the art. In a further preferred embodiment, said fusion protein comprises a peptide or polypeptide comprising the amino acid sequence of an immunogenic protein, preferably an immunogenic protein of a pathogenic microorganism, more preferably an EBV protein, most preferably a latent EBV protein.

It is, however, also envisaged by the present invention that one or more non-essential EB-viral polypeptides is or are lacking from the EB-VLP. In the context of the present specification, "non-essential EBV polypeptide" relates to a polypeptide incorporated into wildtype EB-viral particles but not essential for the formation of VLPs. A polypeptide is non-essential if VLPs are detectable by electron microcopy or one of the other methods described in the examples of the present specification after suitable host cells have been induced to produced to produce VLPs according to the methods of the present specification in the absence of said polypeptide. E.g., the product of the EBV BNRF1 gene, which was shown to play a role in the escape of EBV particles from endosomes after infection (Feederle, R, et al. (2006), Epstein-Barr virus BNRF1 protein allows efficient transfer from the endosomal compartment to the nucleus of primary B lymphocytes. J Virol. 80(19):9435-43) may be lacking from an EB-VLP. The methods how to omit a polypeptide from a host cell during lytic infection of EBV are well-known to the skilled artisan. Preferably, a polypeptide is omitted by deleting the gene coding for said polypeptide from the viral genome or by rendering said gene unexpressible by means of genetic manipulation, e.g. by mutating the start codon to a non-start codon.

The term "substantially free of EBV DNA" as used herein will be understood by those skilled in the art. That said term does not necessarily mean that all EB-VLPs are free of EBV DNA. The term, however, requires that the number of EBV DNA free EB-VLPs produced by the method of the invention is increased by a statistically significant portion compared to control EB-VLPs. Control VLPs are delTR-EBV VLPs as described herein above. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. The p-values are, preferably, 0.1, 0.05, 0.01, 0.005, or 0.0001. Further, the number of EBV DNA containing EB-VLPs produced by the method of the present invention is preferably decreased by at least fivefold, at least tenfold, at least 20 fold, at least 50 fold, at least 100 fold, at least 1000 fold, or at least 10000 fold compared to control EB-VLPs.

Preferably, EB-VLPs substantially free of EBV DNA are EB-VLPs containing less than 10000 EBV genomes/ml supernatant, more preferably less than 1000 EBV genomes/ml supernatant, even more preferably less than 100 EBV genomes/ml supernatant, and most preferably less than 10 EBV genomes/ml supernatant (when produced and assayed in the PCR assay as described in the examples of the current specification. Preferably, the number of EBV genomes is less than $200/10^6$ EBV-VLPs, less than $100/10^6$ EBV-VLPs, less than $50/10^6$ EBV-VLPs, less than $20/10^6$ EBV-VLPs, less than $10/10^6$ EBV-VLPs, less than $1/10^6$ EBV-VLPs, less than $0.1/10^6$ EBV-VLPs, or less than $0.01/10^6$ EBV-VLPs.

Preferably, EB-VLPs substantially free of EBV DNA are EB-VLPs establishing latent infection in Raji cells at a rate of less than 10 infected cells/ml supernatant, more preferably less than 1 infected cell/ml supernatant, even more preferably less than 0.1 infected cells/ml supernatant, most preferably less than 0.01 infected cells/ml supernatant when produced and assayed in the infection assay as described in the examples of the current specification. Preferably, the rate is less than 10 infected Raji cells/$10^6$ EB-VLPs, more preferably less than 1 infected cell/$10^6$ EB-VLPs, even more preferably less than 0.1 infected cells/$10^6$ EB-VLPs, most preferably less than 0.01 infected cells/$10^6$ EB-VLPs.

Preferably, the EB-VLPs of the present invention are used as a medicament. The term "use as a medicament" as used herein relates to the use of EB-VLP as an agent in the diagnosis, cure, treatment, or prevention of disease.

Also preferably, the EB-VLPs of the present invention are used for vaccination. "Vaccination", as used herein, relates to the administration of antigenic material to stimulate the immune system of a subject to develop adaptive immunity. Vaccination is therapeutic or prophylactic vaccination.

Therapeutic vaccination refers to vaccination in order to ameliorate or cure a disease or a disorder referred to herein or the symptoms accompanied therewith to a significant extent. Therapeutic vaccination may lead to an entire restoration of the health with respect to the diseases or disorders referred to herein. It is to be understood that therapeutic vaccination as used in accordance with the present invention may not be effective in all subjects. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

Prophylactic vaccination relates to vaccination in order to retaining health with respect to the diseases or disorders referred to herein for a certain period of time, preferably life-long, in a subject. It will be understood that the said period of time is dependent on the amount of the EB-VLPs which has been administered and individual factors of the subject discussed elsewhere in this specification. It is to be understood that prophylactic vaccination may not be effective in all subjects treated with the EB-VLP according to the present invention. However, the term requires that a statistically significant portion of subjects of a cohort or population are effectively prevented from suffering from a disease or disorder referred to herein or its accompanying symptoms. Preferably, a cohort or population of subjects is envisaged in this context which normally, i.e. without prophylactic vaccination according to the present invention, would develop a disease or disorder as referred to herein. Whether a portion is statistically significant can be determined without further ado by the person skilled in the art using various well known statistic evaluation tools discussed elsewhere in this specification.

The definitions made above apply mutatis mutandis to the following:

In a further embodiment, the present invention relates to a polynucleotide comprising an EBV genome a) lacking at least one expressible gene selected from the group consisting of the BFLF1 gene, the BBRF1 gene, the BGRF1 gene, the BDRF1 gene, the BALF3 gene, the BFRF1A gene, and the BFRF1 gene, and b) being capable of producing the EB-VLP of present invention in a suitable host cell.

The term "polynucleotide" as used herein refers to a linear or circular nucleic acid molecule. The polynucleotide of the present invention shall be provided, preferably, either as an isolated polynucleotide (i.e. isolated from its natural context) or in genetically modified form. The term encompasses single as well as double stranded polynucleotides. Moreover, comprised are also chemically modified polynucleotides including naturally occurring modified polynucleotides such as glycosylated or methylated polynucleotides or artificially modified derivatives such as biotinylated polynucleotides.

The polynucleotide of the present invention comprises an EBV genome lacking at least one expressible gene selected from the group consisting of the BFLF1 gene (gene for EBV type 1: SEQ ID NO: 3; protein product SEQ ID NO: 4, Genbank Acc. No: YP_401648.1 GI:82503206; gene for EBV type 2: SEQ ID NO: 5; protein product SEQ ID NO: 6, Genbank Acc. No: YP_001129444.1 GI:139424479), the BBRF1 gene (gene for EBV type 1: SEQ ID NO: 7; protein product SEQ ID NO: 8, Genbank Acc. No: YP_401682.1 GI:82503238; gene for EBV type 2: SEQ ID NO: 9; protein product SEQ ID NO: 10, Genbank Acc. No: YP_001129476.1 GI:123811640), the BGRF1/BDRF1 gene (gene for EBV type 1: SEQ ID NO: 11, protein product SEQ ID NO: 12, Genbank Acc. No: YP_401690.1 GI:82503246; gene for EBV type 2: SEQ ID NO: 13; protein product SEQ ID NO: 14, Genbank Acc. No: YP_001129485.1 GI:139424519), the BALF3 gene (gene for EBV type 1: SEQ ID NO: 15; protein product SEQ ID NO: 16, Genbank Acc. No: YP_401715.1 GI:82503271; gene for EBV type 2: SEQ ID NO: 17; protein product SEQ ID NO: 18, Genbank Acc. No: YP_001129509.1 GI:139424543), the BFRF1A gene (gene for EBV type 1: SEQ ID NO: 19; protein product SEQ ID NO: 20, Genbank Acc. No: YP_401728.1 GI:82503279; gene for EBV type 2: SEQ ID NO: 21; protein product SEQ ID NO: 22, Genbank Acc. No: YP_001129445.1 GI:139424480), and the BFRF1 gene (gene for EBV type 1: SEQ ID NO: 23; protein product SEQ ID NO: 24, Genbank Acc. No: YP_401649.1 GI:82503207; gene for EBV type 2: SEQ ID NO: 25; protein product SEQ ID NO: 26, Genbank Acc. No: YP_001129446 GI:139424481). The products of said genes are proteins with an activity essential for the packaging of viral DNA into procapsids of EBV, thus removal of their function leads to production of the EB-VLP of the present invention. The term "lacking an expressible gene" relates to an EBV genome in which at least one gene selected from the group as defined supra has been modified such that a functional protein product can not be expressed. This can be accomplished in various ways known to the skilled person and detailed in the examples below.

Preferably, at least one of the genes supra is modified by introducing a deletion, addition and/or substitution of at least one nucleotide leading to a truncation, disruption or mutation of the protein produced from the said gene. Such modifications encompass point mutations in gene resulting in the generation of a stop codon as well as modifications resulting in a shift of the open reading frame. Such polypeptides being created are abnormally short or abnormally long and have no biological function. Also encompassed are point mutations in gene which result in a polypeptide with no or with a decreased biological function. Also preferably, a deletion, addition and/or substitution of at least one nucleotide can be, preferably, introduced which leads to an inactivation of the transcriptional control sequence (i.e. the promoter) which governs expression of the gene. Moreover, sequences may be, preferably, introduced which in the transcribed RNA result in increased RNA degradation. More preferably, the entire locus for the at least one the of genes supra is deleted or replaced by a non-functional or non-expressible nucleic acid. Most preferably, the open reading frame is substituted by a selectable marker gene, such as the kanamycin resistance gene as indicated in the Figures and Examples, below.

The test if a given modification of one of the genes supra leads to a non-expressible gene will depend on the nature of the modification introduced as will be known to the skilled artisan. E.g. if a large part of the coding sequence of a gene has been deleted, electrophoretic separation of EBV proteins followed by immunoblotting with an antibody specific for the protein product of said gene will be appropriate, since the product of the gene containing the deletion will have a lower apparent molecular mass. On the other hand, if one of the genes supra is deleted entirely, restriction analysis of the resulting EBV genome may be sufficient. In each case, loss of the function of one of the genes supra can be assayed by detecting EB-VLP of the present invention, i.e. EB-VLP substantially free of EBV DNA according to the methods detailed herein below.

The polynucleotide of the present invention is a polynucleotide comprising an EBV genome with the biological activity of directing production of EB-VLP according to the present invention in a suitable host cell. Suitable assays for measuring said activity are described in the accompanying examples. Preferably, the polynucleotide comprises one of the nucleic acid sequences shown in SEQ ID NO: 27 (an EBV type 1 genome comprising a BFLF1 knockout, i.e. lacking an expressible BFLF1 gene) or in SEQ ID NO: 28 (an EBV type 1 genome comprising a BBRF1 knockout, i.e. lacking an expressible BBRF1 gene).

Moreover, the term "polynucleotide" as used in accordance with the present invention further encompasses variants of the aforementioned specific polynucleotides. Said variants may represent strain or clonal variants of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode an EBV genome having the activity as specified above. A polynucleotide comprising a fragment of any of the aforementioned nucleic acid sequences is also encompassed as a polynucleotide of the present invention. The fragment shall encode an EBV genome which still has the activity as specified above.

The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

Preferably, the polynucleotide of the present invention comprises alterations in addition to the modifications detailed above. Especially, since some of the latent gene products of EBV are known or suspected to have a transforming effect on cells (EBNA2, LMP1, EBNA3A, -B and -C (Hammerschmidt W, Sudgen B (1989) Genetic analysis of immortalizing functions of Epstein-Barr virus in human B-lymphocytes. Nature 340: 393-397; Cohen J I, et al. (1989) Epstein-Barr virus nuclear protein 2 is a key determinant of lymphocyte transformation. PNAS 86:9558-9562; Kaye K M, et al. (1993) Epstein-Barr virus latent membrane protein 1 is essential for B-lymphocyte growth transformation. PNAS, 90, 9150-9154; Tomkinson B, et al. (1993) Epstein-Barr virus nuclear proteins EBNA3A and EBNA3C are essential for B-lymphocyte growth transformation. J. Virol. 62:6762-6771)), it is desirable to remove the genes coding for these transforming proteins from the polynucleotide of the present invention. Also, the BZLF1 gene product is known to be the major activation protein that mediates entry of EBV into its lytic cycle, i.e. the virus-producing part of its life-cycle. It is thus preferable to remove this functionality from the polynucleotide of the present invention in order to avoid virus production from residual genomes applied to a subject, e.g. during vaccination. The methods of functionally deleting said genes are the same as detailed supra. More preferably, at least one, most preferably all of said genes are deleted entirely.

The term "suitable host cell" as used herein relates to a cell capable of facilitating lytic replication of EBV, leading to the production of EB-VLPs. Preferably, said cell is a mammalian cell, more preferably a primate cell, even more preferably a human cell. Most preferably, the host cell is a 293 cell. It is also envisaged by the current invention that the host cell may provide certain factors essential for lytic replication of EBV. E.g. where an EBV genome lacking a functional BZLF1 gene is used, which causes the virus to be unable to enter the lytic cycle, such function may be provided by the host cell after an expression construct for said BZLF1 gene has been transfected into the cell.

The methods for generating said modifications are well known to the person skilled in the art and include gene targeting methods based on homologous recombination, PCR-based mutagenesis, chemical mutagenesis using agents such as ENU or EMS, mutagenesis by irradiation and others. In particular, the entire gene locus can be deleted by homologous recombination as described in the accompanying Examples below.

In another preferred embodiment, the present invention relates to a vector comprising the polynucleotide of the present invention. Preferably, the vector is a plasmid or viral vector capable of stably maintaining an EBV genome in a cell. More preferably, the vector is derived from the *Escherichia coli* (*E. coli*) F-Plasmid; these vectors are known to the skilled person as F-factor based replicon or bacterial artificial chromosome (BAC), which allow for stably maintaining a complete EBV genome in *E. coli* bacterial cells. Moreover, the term also relates to targeting constructs which allow for random or site-directed integration of the targeting construct into genomic DNA. Such target constructs, preferably, comprise DNA of sufficient length for either homologous recombination or heterologous insertion.

The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. Vectors and transformation or transfection techniques are well known in the art and can be applied by the person skilled in the art without further ado. For example, a BAC plasmid vector can be introduced into *E. coli* cells by electroporation, or into mammalian cells in a complex with charged lipids.

In another preferred embodiment, the present invention relates to a host cell comprising the polynucleotide or the vector of the present invention.

Host cells as referred to herein encompass eukaryotic cells as well as prokaryotic cells. In particular, prokaryotic cells referred to in accordance with the present invention may be bacterial cells that can be used for the propagation of, e.g., the polynucleotide or vector of the present invention. Preferred bacteria for this purpose are *E. coli* bacteria, more preferably strain DH10B. Eukaryotic cells are, preferably, cells which are capable of expressing genes of the EBV genome comprised in the polynucleotide or vector of the invention. Preferred cells expressing genes of the latent cycle of the EBV life cycle are, e.g., Raji cells. More preferably, said cells are capable of assembling Epstein-Barr virus like particles (EBV-VLP), i.e. suitable host cells as described above.

In another preferred embodiment, the present invention relates to a method for manufacturing EB-VLPs substantially free of EBV DNA, comprising the steps of a) culturing a suitable host cell comprising the polynucleotide or the vector of the present invention, and b) obtaining EB-VLPs substantially free of EBV DNA from the cells.

The method of the present invention, preferably, is an in vitro method. Moreover, it may comprise steps in addition to those explicitly mentioned above. For example, further steps may relate to pre-treatments of suitable host cells or post-treatments of harvested supernatants comprising EB-VLPs.

The term "culturing" is known by the person skilled in the art. Particularly, the term relates to cells growing outside the organism in a cell culture medium. The term also relates to the process of growing cells in culture outside the organism. Suitable cell culture media are known by the person skilled in the art and are commercially available. They may comprise nutrients, salts, growth factors, antibiotics, serum (e.g. fetal calf serum) and pH-indicators (e.g. phenol red). Preferably, the method further comprises the step of expressing at least one gene coding for an artificial polypeptide as described herein above in the suitable host cell, leading to the incorporation of said artificial polypeptide into the EB-VLPs.

The term "obtaining" refers to an isolation and/or purification step known to the person skilled in the art. Preferably, after said isolation and/or purification the EB-VLPs exhibit a purity of at least 80%, preferably 80%-90%, more preferably 90%-97%, most preferred more than 97% up to an absolute pure form without any contamination. The term "purification" encompasses means and methods such as chromatographic devices. Preferably used methods may include density gradient centrifugation, size-exclusion chromatography, affinity chromatography, and precipitation and columns. Preferably, obtaining EB-VLPs includes purification of EB-VLPs by binding them to magnetic beads via anti-gp350 antibodies as described in the examples herein below. Preferably, EB-VLP are obtained from the supernatant of suitable host cells, i.e. the EB-VLPs are released into the medium during the method of the present invention.

In a preferred embodiment, the present invention relates to a method for the manufacture of a vaccine comprising the steps of the method of the present invention and the further step of formulating the EB-VLPs as a vaccine. In another preferred embodiment, the present invention relates to a vaccine containing EB-VLPs substantially free of EBV DNA obtainable by the method according the present invention.

The term "vaccine" as used herein, preferably, relates to a composition comprising EB-VLPs substantially free of DNA according to the present invention which—when administered to an animal, preferably a human-elicits an immune response against EBV. Thus, administering said vaccine stimulates the immune system and establishes or improves immunity to infection with EBV. Preferably, the vaccine according to the present invention allows for establishing or improving immunity to infection with EBV. Preferably, the immunization causes activation and expansion of T-cells and/or B-cells specifically recognizing structural EBV antigens. More preferably, immunization causes the production of antibodies preventing infection of body cells by EBV.

The vaccine of the invention, preferably, further comprises one or more pharmaceutically acceptable carrier as described in detail below. The vaccine of the present invention can be formulated as pharmaceutically acceptable salt. The vaccines are, preferably, administered topically or systemically. Suitable routes of administration conventionally used for drug administration are oral, intravenous, or parenteral administration as well as inhalation. However, depending on the nature and mode of action of a compound, the vaccines may be administered by other routes as well. Moreover, the compounds can be administered in combination with other vaccines either in a common vaccine or as separated vaccines wherein said separated vaccines may be provided in form of a kit of parts.

The compounds are, preferably, administered in conventional dosage forms prepared by combining the EB-VLPs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

A therapeutically effective dose refers to an amount of the compounds to be used in a vaccine of the present invention which induces immunization according to the present specification. The dosage regimen will be determined by the attending physician and other clinical factors, preferably in accordance with any one of the above described methods. As is well known in the medical arts, dosages for any one patient may depend upon several factors, including the patient's age, the particular compound to be administered, sex, time and route of administration, general health, and other drugs being administered concurrently. Immunization can be monitored by periodic assessment. A typical dose can be, for example, in the range of 1 to 1000 μg; however, doses below or above this exemplary range are envisioned, especially considering the aforementioned factors.

The vaccines and formulations referred to herein are administered at least once in order to treat or ameliorate or prevent a disease or condition recited in this specification. However, the said vaccines may be administered more than one time, for example up to four times.

Specific vaccines are prepared in a manner well known in the pharmaceutical art and comprise at least EB-VLPs in admixture or otherwise associated with a pharmaceutically acceptable carrier or diluent. For making those specific vaccines, the EB-VLPs will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

In a further preferred embodiment said composition further comprises at least one pharmaceutically acceptable carrier and/or at least one excipient. It is to be understood that the carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like.

The diluent(s) is/are selected so as not to affect the biological activity of the combination. Examples of such diluents are distilled water, physiological saline, Ringer's solutions, dextrose solution, and Hank's solution. In addition, the vaccine or formulation may also include other carriers, excipients, or nontoxic, nontherapeutic, nonimmunogenic stabilizers and the like. Said nontoxic, nontherapeutic, nonimmunogenic stabilizers are well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

A preferred further component of the composition is an excipient. Excipients are compounds which may not elicit an immune response when administered to the host alone but which may further enhance the immune response of the host when administered together with the immunogenic polypeptides. It is known in the art that excipients may act as surfactants which promote concentration of immunogenic polypeptides over a large surface area, or may have immunostimulatory properties.

In another preferred embodiment, the present invention relates to a composition comprising Epstein-Barr virus like particles (EB-VLPs) substantially free of EBV DNA obtainable by the method of the invention for use as a vaccine for the treatment and/or prevention of disease.

The term "use as a vaccine for the treatment" relates to the use of the vaccine of the present invention as a therapeutic vaccine as specified herein above. Likewise, the term "use as a vaccine for the prevention" relates to the use as a prophylactic vaccine.

The term "subject" relates to a metazoan organism with the capacity to generate an immune response to molecules foreign to the organism. Preferably, the subject is an animal, more preferably a mammal, most preferably a human being.

As used herein, the term "EBV-related disease" relates to all disorders caused by the infection of a subject by EBV. In a preferred embodiment said EBV-related disease is infectious mononucleosis, Hodgkin's Lymphoma, Burkitt's Lymphoma, nasopharyngeal carcinoma, rheumatoid arthritis, multiple sclerosis, systemic lupus erythematosus, gastric carcinoma, or post-transplant lymphoproliferative disorder. The symptoms which characterize these diseases are well known in the art and are described in standard text books of medicine.

All references cited throughout this specification are herewith incorporated by reference with respect to their specific disclosure content mentioned above as well as in their entirety.

FIGURES

FIG. 1. Construction of the EBV ΔBFLF1 and ΔBBRF1 recombinant viruses.

The left panel represents the schematic restriction map of the EBV genome region that contains the BFLF1 or BBRF1 genes before and after introduction of the mutation. The locations of the BamHI and HindIII restriction sites are indicated. Most of the BFLF1 or BBRF1 open reading frames were substituted against a kanamycin resistance gene. In the case of BFLF1 deletion this led to the exchange of a 7.4 kb BamHI fragment against a 7.5 kb BamHI fragment or substitution of a 29.3 kb HindIII fragment through a combination of a 9.1 kb and of a 20.2 kb HindIII fragments. A 9.7 kb BamHI fragment in the locus of BBRF1 gene was replaced by a 10.3 kb one and a 25.9 kb HindIII fragment was substituted against two fragments with sizes 23 kb and 3.6 kb respectively. The right panel shows the restriction fragment analysis of wild type and ΔBFLF1 or ΔBBRF1 mutant viruses. Viral DNA was isolated from E. coli and producer 293 cell lines and digested with two different enzymes. Restriction fragments modified by the deletion of the corresponding genes are indicated.

Figure 2:
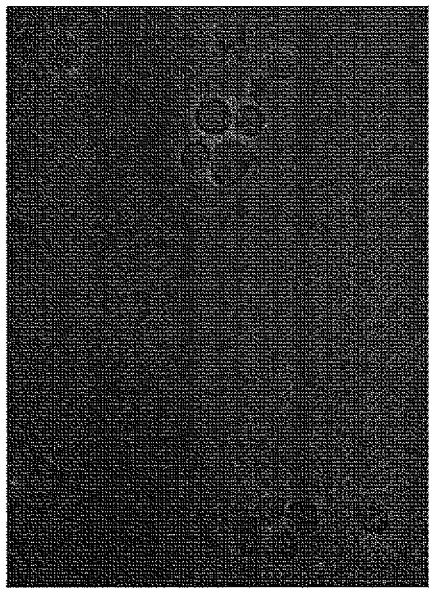
Figure 2:
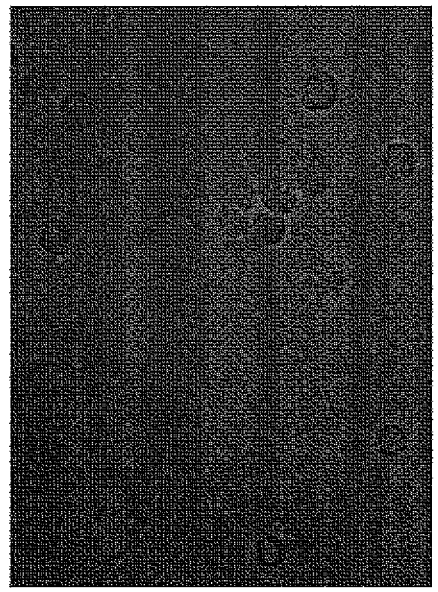
Figure 2:
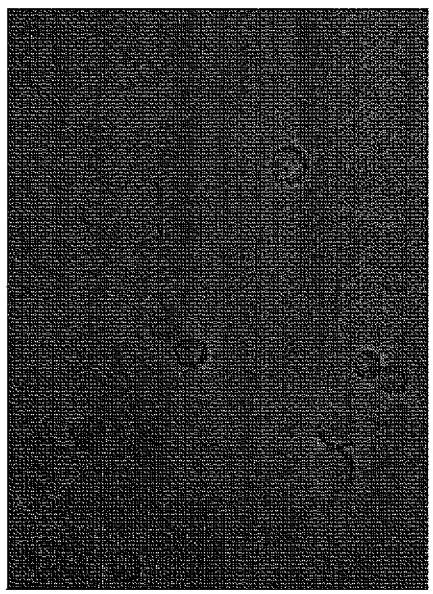
Figure 2:
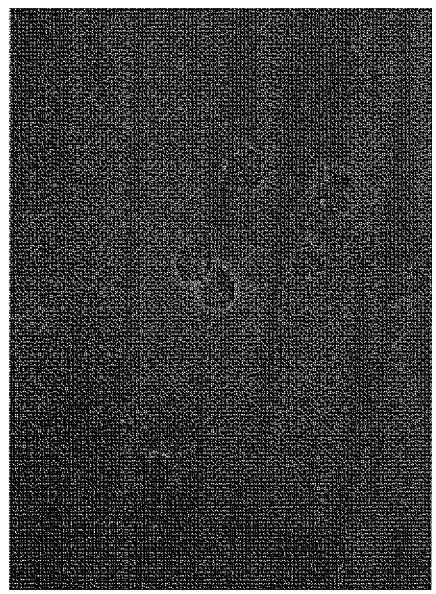

FIG. 2. Immunostaining of VLPs and virions in supernatants from induced producer cells.

Supernatants from producer cell lines containing either wild type viruses or mutants devoid of BFLF1, BBRF1 or of the terminal repeats were admixed for one hour at 4° C. with an EBV-negative B cell line. Viruses bound to the B cells were immunostained with a gp350-specific antibody, followed by a Cy3-coupled secondary anti-mouse antibody.

Figure 3:
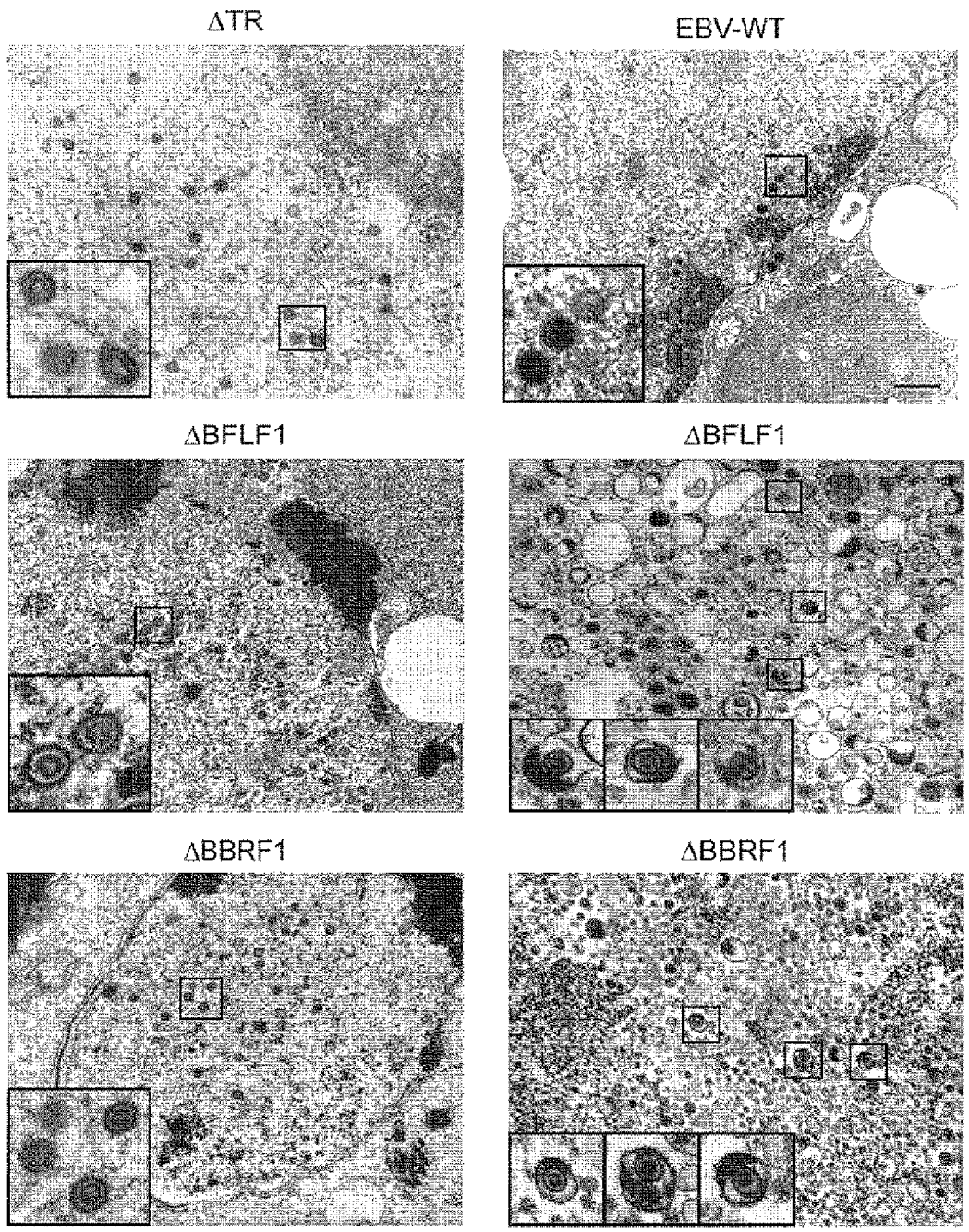

FIG. 3. Electron micrographs of 293 cells that contain ΔBFLF1, ΔBBRF1, ΔTR or EBV wild type genomes.

Electron micrographs of 293 cells that contain ΔBFLF1, ΔBBRF1, ΔTR or EBV wild type genomes after induction of the virus lytic replication, electron micrographs showing VLPs in pelleted supernatants from ΔBFLF1 or ΔBBRF1 mutants. Examination revealed an abundance of A- and B-capsids in preparations from ΔBFLF1, ΔBBRF1 and ΔTR viruses. Infectious DNA-filled mature C-capsids were observed in cells that contain the wild type virus but not in those that contain mutants. Inset bars, 200 nm.

Figure 4:
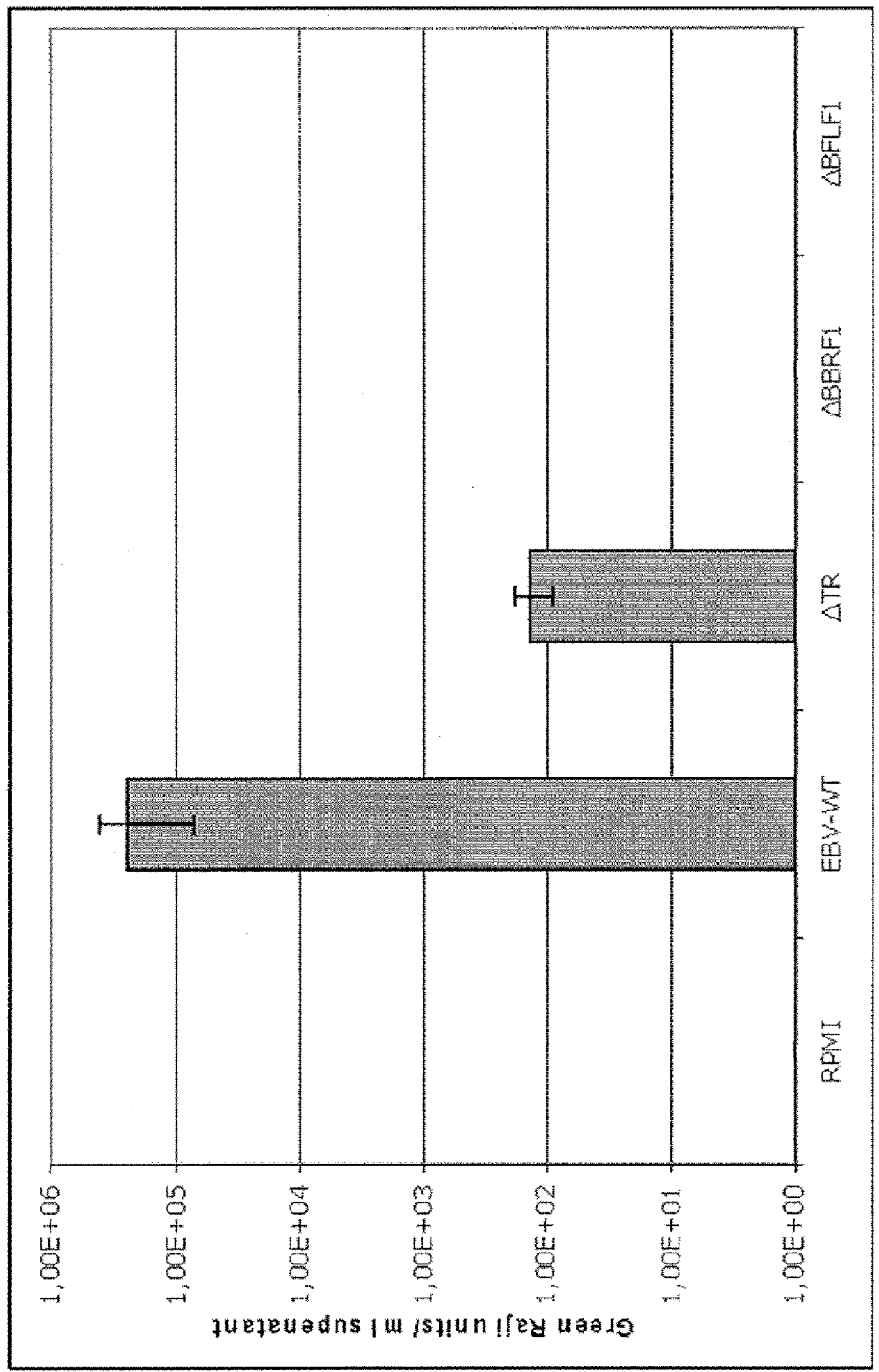

FIG. 4. Infection of Raji B-cells with ΔBFLF1, ΔBBRF1, ΔTR or wild type viruses.

The ability of mutants and wild type viruses to infect the Raji B cell line is indicated. The observed titers are given as the number of EBV-infected Raji cells, or green Raji units, per ml of supernatant.

Figure 5:
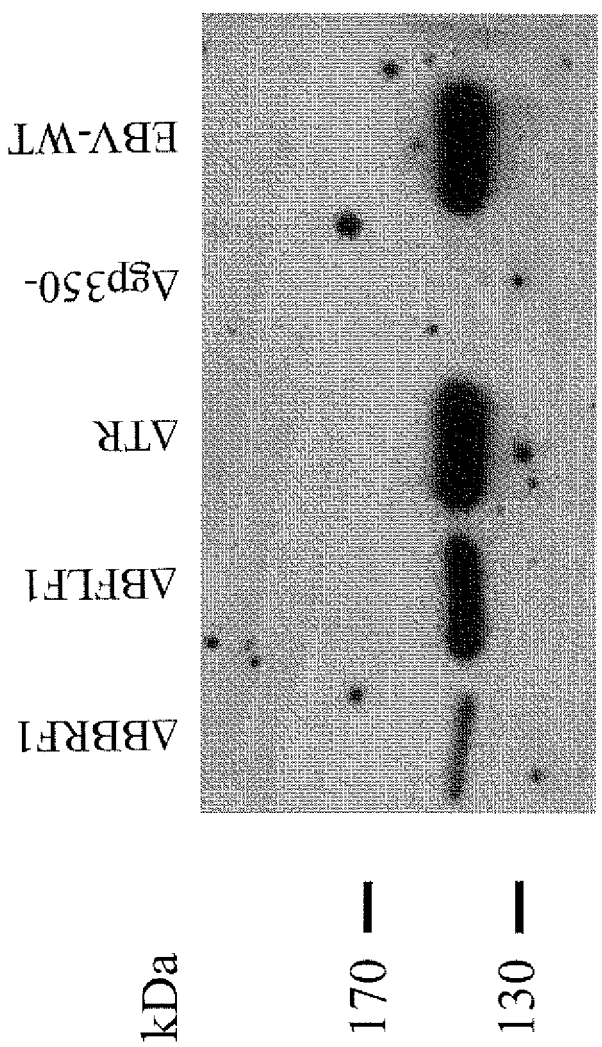

FIG. 5. Western blot analysis using immunopurified VLPs.

Gp350 is a viral glycoprotein present in the viral envelope of mature particles. We used a monoclonal antibody specific to gp350 coupled to magnetic Dynabeads to purify EBV virions or VLPs from infectious supernatants. Supernatants from induced wild type or different mutant producer cell lines were incubated with the coupled beads for 1 h at room temperature. Bound virus particles were collected with a magnet, washed 3 times with RPMI and used for detection of viral proteins or viral DNA. A Western blot analysis was performed on immunopurified VLP/virions using an antibody specific to the EBV tegument protein BNRF1 (140 kDa). BNRF1 was detected in wild type virions, but also in supernatants from induced producer cell lines that contain ΔBFLF1, ΔBBRF1 or ΔTR mutants. Mutant viruses that lack gp350 (Δgp350) were used as a negative control in the purification experiment.

Figure 6:
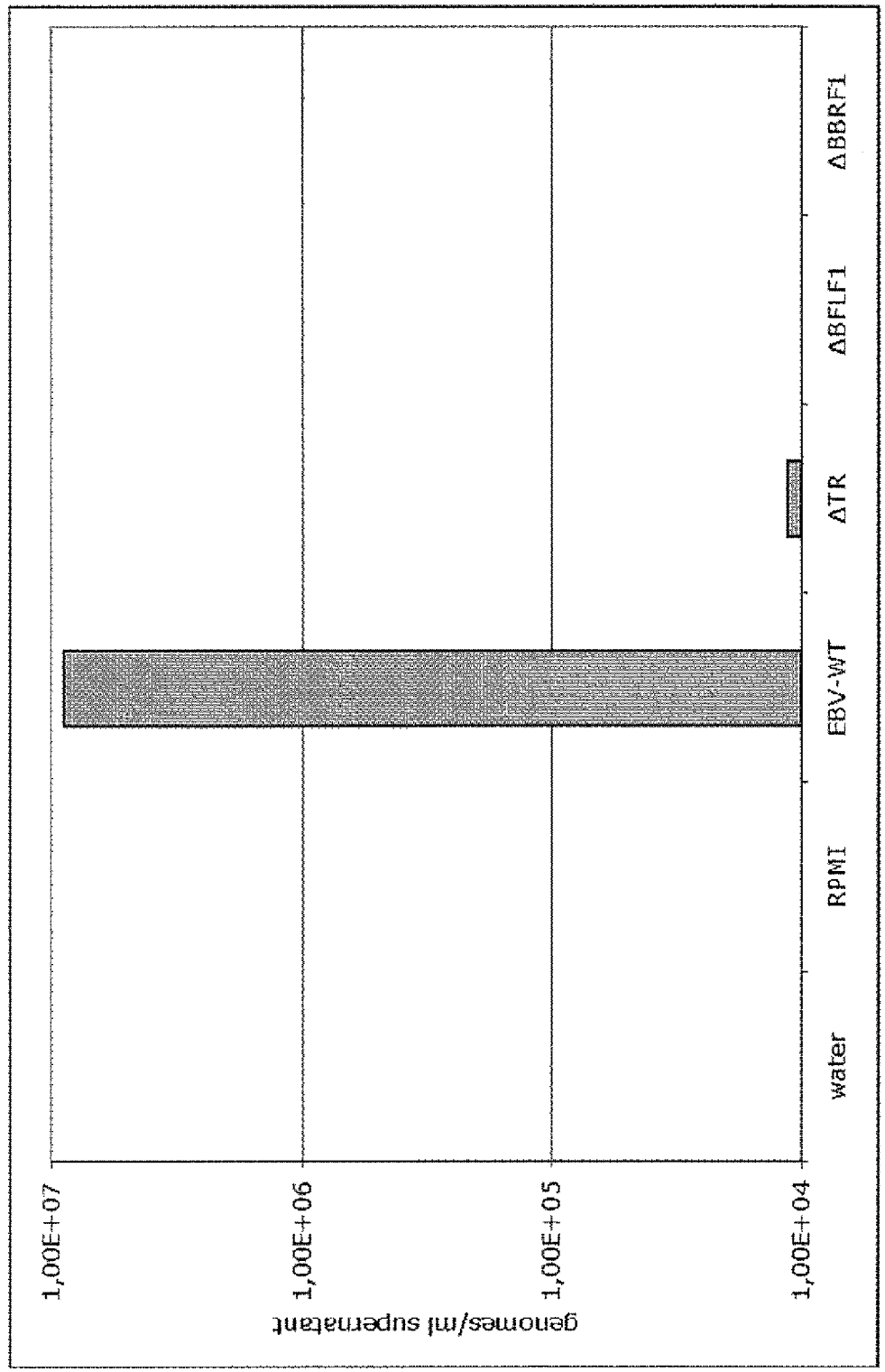

FIG. 6. Quantitative PCR (qPCR) analysis using immunopurified VLPs.

VLP or virions purified with the gp350-specific antibody were assessed for the presence of viral DNA using qPCR with primer and probes specific for the viral polymerase gene. Wild type viruses were used as positive controls. Virus titers are given as genome equivalents per ml supernatant.

Figure 7:
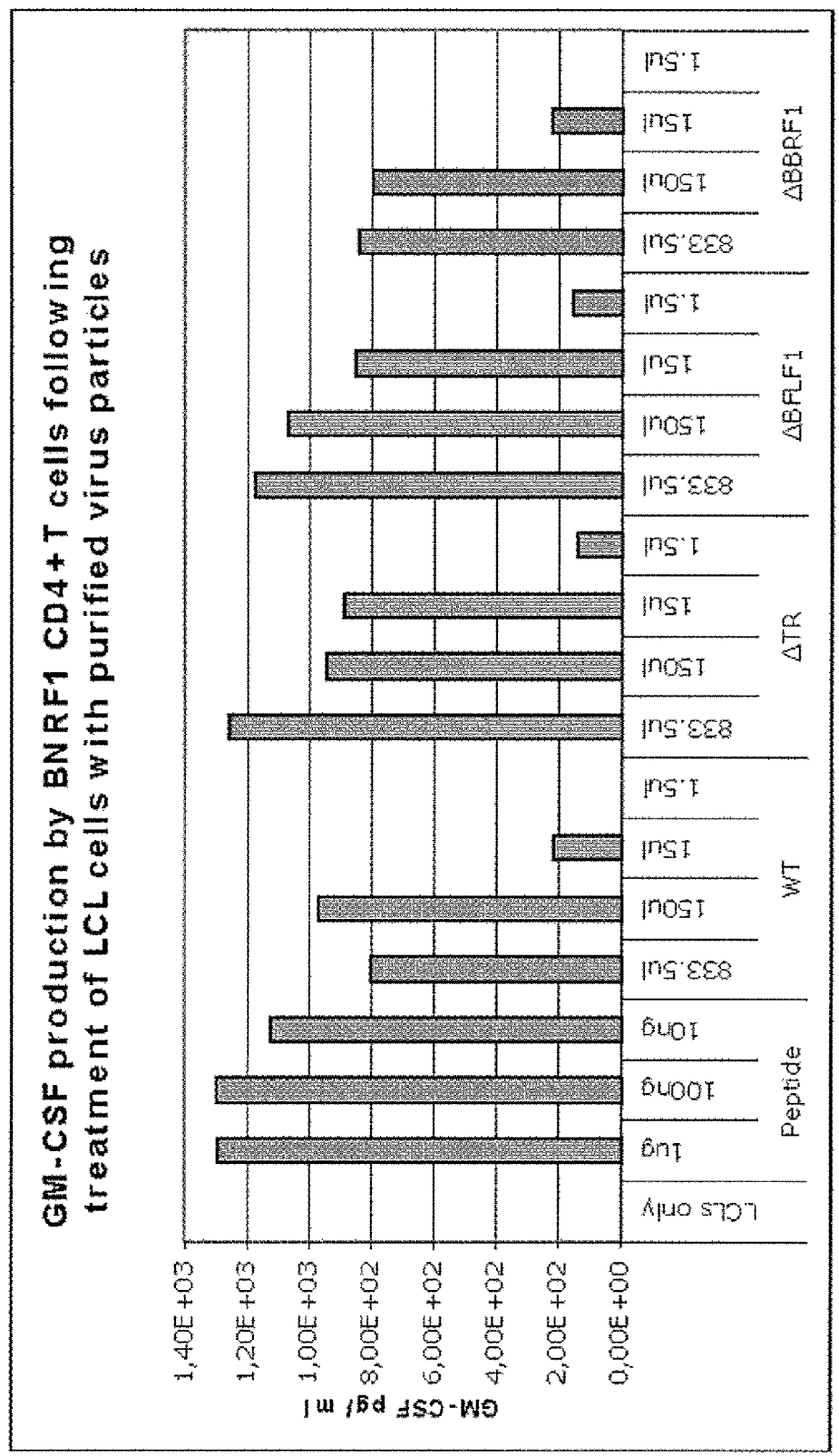

FIG. 7. B cells pulsed with ΔBFLF1 and ΔBBRF1 VLPs are recognized by EBV specific T cells.

Virus particles present in 1 ml of the indicated virus supernatants were purified using gp350 antibodies, coupled to magnetic beads and resuspended in fresh medium. LCL cells were pretreated with indicated amounts of BNRF1 peptide or volumes of purified virus particles. The pulsed LCLs were incubated with BNRF1 CD4+ T-cells and production of GM-CSF was measured by ELISA.

Figure 8:
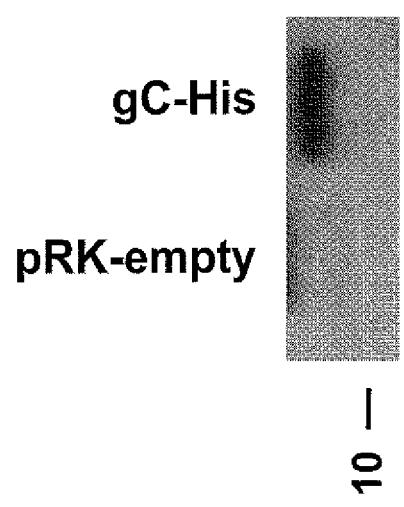

FIG. 8. VLPs can incorporate foreign proteins.

A plasmid that encodes the intracytoplasmic and transmembrane domain of the glycoprotein gC from herpes simplex virus fused in frame with 6 successive histidines (gC-6× his) was transfected into the ΔBFLF1 producer cell line upon initiation of the EBV lytic replication. Produced virus particles were purified using gp350 antibodies coupled to dynabeads and analysed in western blot. Only viruses that were obtained from 293/ΔBFLF1 cells transfected with the gC-6× his have incorporated this protein.

Figure 9:
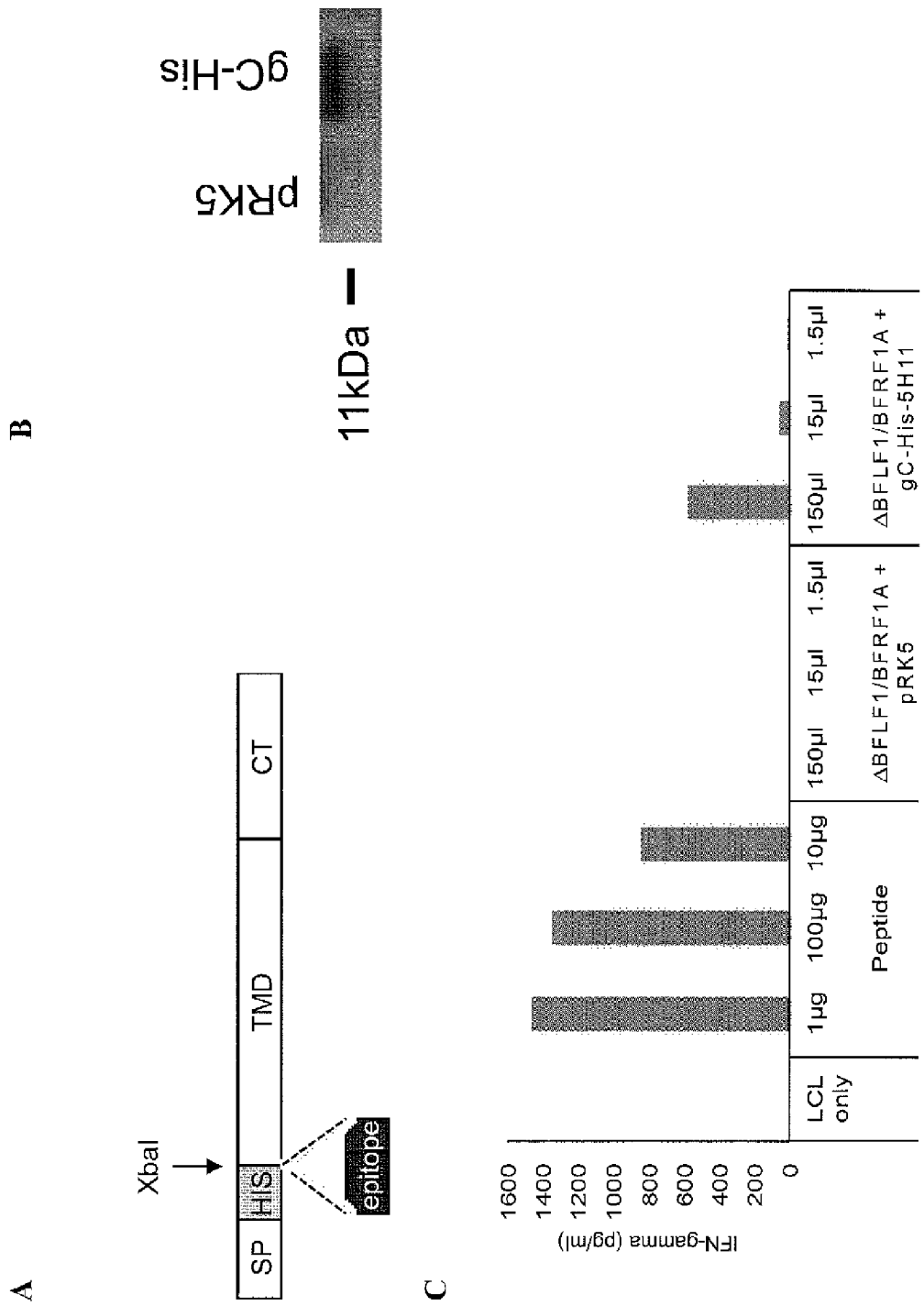

FIG. 9. Inserting gC fusion proteins into the LP/VLP envelope and evaluation of the particle immune efficiency. (A) Schematic of the proposed HSV1-gC-EBV fusion protein constructs. (SP, gC signal peptide; His, His-tag; epitope, EBV T cell epitope; TMD, gC transmembrane domain; and CT, gC cytoplasmic tail). (B) Western blot showing expression of His-tagged gC fusion proteins in LPs/VLPs. LPs/VLPs were generated from an EBV mutant producer cell line that was induced in the presence of plasmid encoding the gC fusion protein, or pRK5 as a negative control. A His-specific antibody was used. (C) EBNA3C 5H11 epitope specific T-cell activation after incubation of LCLs with supernatants from lytically induced mutant producer cells in presence of gC-His-5H11 fusion protein expression plasmid or pRK5 empty plasmid. ELISA was used to determine the IFN-gamma secretion.

The following Examples shall merely illustrate the invention. They shall not be construed, whatsoever, to limit the scope of the invention.

EXAMPLES

Example 1

Construction of the EBV ΔBFLF1 and ΔBBRF1 Recombinant Viruses

The EBV ΔBFLF1 and ΔBBRF1 viruses were obtained by exchanging most of the corresponding open reading frames present on the EBV B95.8-BAC recombinant plasmid (Proc Natl Acad Sci USA. 1998 Jul. 7; 95(14):8245-50. Propagation and recovery of intact, infectious Epstein-Barr virus from prokaryotic to human cells. Delecluse H J, Hilsendegen T, Pich D, Zeidler R, Hammerschmidt W.) (EBV B95.8 strain co-ordinates #57131-58568 for BFLF1 and #114204-116042 for BBRF1 (accession number V01555)) against a kanamycin/neomycin cassette flanked by frt sites (co-ordinates #57131-58673 in ΔBFLF1 and 114501-116042 in ΔBBRF1) using RecA-mediated homologous recombination in E. coli. The viral genomes that properly eliminated BFLF1 or BBRF1 were selected with kanamycin. Candidate clones were analysed by plasmid minipreparation coupled to restriction analysis using the HindIII and BamHI restriction enzymes to confirm their structure (FIG. 1). Sequencing confirmed that the targeted open reading frames had been deleted and that the recombination took place like expected.

Example 2

Generation of 293/ΔBFLF1 and 293/ΔBBRF1 Cells

The EBV ΔBFLF1 and ΔBBRF1 DNA respectively was then transfected into 293 cells and selected for hygromycin resistance; the EBV-BAC recombinant carries the hygromycin resistance gene and therefore allows selection of cells stably transfected with the recombinant DNAs. EBV ΔBFLF1 or ΔBBRF1 genomes present in the 293 Hygromycin resistant clones were purified and transferred back into E. coli cells. From these bacterial cells, EBV ΔBFLF1 or ΔBBRF1 plasmids were prepared to confirm their identity and their integrity. One of each clones, referred to as 293/ΔBFLF1 or 293/ΔBBRF1 respectively were selected for further experiments. Transient transfection of an expression plasmid that encodes the BZLF1 transactivator allow initiation of lytic replication and therefore production of infectious viruses or of non-infectious VLPs. Controls included 293 cells that contain wild type viruses. Three days after transfection viral supernatants from 293/ΔBFLF1 and 293/ΔBBRF1 cells were incubated with cells from the EBV-negative Elijah B cell line (FIG. 2). Because EBV virions bind to B cells, viruses bound at the surface of B cells can be revealed by an immunostaining using antibodies directed against gp350, a component of the viral envelope. This experiment confirmed that supernatants from induced either 293/ΔBFLF1 or 293/ΔBBRF1 cells contain gp350 positive viral structures that bind to B cells and could represent either VLPs or mature virions. Similar results were obtained with a 293 clone that contains wild type viruses. 293 cells that contain a recombinant virus that lacks the terminal repeats, a viral sequence that is used as packaging signals (293/ΔTR) (Proc Natl Acad Sci USA. 1999 Apr. 27; 96(9):5188-93. A first-generation packaging cell line for Epstein-Barr virus-derived vectors. Delecluse H J, Pich D, Hilsendegen T, Baum C, Hammerschmidt W.) was also investigated. We previously showed that 293/ΔTR produces VLPs (first generation VLPs) and this cell line was therefore used as a positive control for the detection of these viral structures (J Virol. 2005 June; 79(12):7641-7. Defective infectious particles and rare packaged genomes produced by cells carrying terminal-repeat-negative epstein-barr virus. Feederle R, Shannon-Lowe C, Baldwin G, Delecluse H J.). We could confirm that supernatants from induced 293/ΔTR contain viral structures that bind to the Raji cell surface.

Example 3

Electron Microscopic Analysis of 293 Cells that Contain ΔBFLF1, ΔBBRF1, ΔTR or EBV Wild Type Genomes Further information about the structure of the viral particles present in the supernatants from induced 293/ΔBFLF1 and 293/ΔBBRF1 was provided by direct observation of both BZLF1-induced mutant producer cells and of pelleted supernatants thereof using electron microscopy (FIG. 3). Electron micrographs either from induced 293/ΔBFLF1 or from 293/ΔBBRF1 cells show that they contain immature EBV virions devoid of viral DNA. Similarly, pelleted 293/ΔBFLF1 and 293/ΔBBRF1 supernatants contain mature EBV virions devoid of viral DNA, ie they represent VLPs. In contrast, 293 cells that contain wild type EBV genomes show EBV particles at various stages of maturation, some of which contain electron-dense cores that correspond to packaged EBV DNA. Wild type EBV virions isolated from supernatants were also found to contain viral DNA. Analysis of 293/ΔTR and their supernatants confirmed that these cells abundantly produce VLPs as expected.

Example 4

Infection of Raji B Cells with the ΔBFLF1 and with the ΔBBRF1 Viruses

In a further attempt to characterize the infection properties of the viral structures produced by induced 293/ΔBFLF1 and 293/ΔBBRF1 cells, we incubated Raji cells with increasing 5-fold dilutions of supernatants from the cell line in 96-well cluster plates, including undiluted supernatant. Three days after infection, GFP-positive Raji cells were counted using a fluorescent microscope. The Raji B cell line is highly susceptible to EBV infection and expresses the green fluorescence protein (GFP) upon infection with the recombinant EBV DNA. Indeed, the GFP gene is cloned onto the recombinant EBV DNA and becomes expressed upon infection of eukaryotic cells. After incubation of Raji cells with one ml of supernatant from induced 293/ΔBFLF1 and 293/ΔBBRF1 no Raji infection could be detected (FIG. 4). In contrast, the same volume of supernatants from induced wild type 293/EBV cells contained enough infectious viruses to generate approximately $2 \times 10^4$ gfp-positive Raji cells. Supernatants from induced 293/ΔTR cells were two orders of magnitude less infectious than wild type viruses but nevertheless generated 120 EBV-positive cells per ml of supernatant and therefore contained 120 infectious particles per ml.

Example 5

Detection of Viral Proteins and Quantification of Viral DNA in EBV ΔBFLF1 and ΔBBRF1 VLPs Gp350 is a major component of mature EBV particles. Viral structures present in supernatants from induced 293/ΔBFLF1, 293/ΔBBRF1, 293/ΔTR, 293/WT were incubated with antibodies specific to gp350, coupled to magnetic dynal beads. Viral structures were then collected with a magnet and the same samples submitted to both western blot and qPCR analysis.

For western blot analysis (FIG. 5), purified viral structures from one ml of supernatant were resuspended in PBS and denatured in Laemmli buffer for 5 minutes at 95° C. The whole sample was separated on a 10% SDS-polyacrylamide gel and electroblotted onto a Hybond ECL membrane (Amersham). After preincubation for 30 min in 5% milk powder in PBS, blots were incubated with a rabbit polyclonal serum against BNRF1 (Feederle et al. (2006), Epstein-Barr virus BNRF1 protein allows efficient transfer from the endosomal compartment to the nucleus of primary B lymphocytes, J Virol; 80(19):9435-43) for 1 h at room temperature. BNRF1 is a tegument protein present at high concentration in EBV viral structures. After several washings in 0.1% Tween in PBS, blots were incubated for 1 h with protein A coupled with horseradish peroxidase. Antibody binding was revealed using an ECL detection reagent (Perkin Elmer). This experiment confirmed the presence of BNRF1-positive viral structures in all three tested supernatants (FIG. 5).

To assess the presence of viral DNA (FIG. 6), the same amount of gp350-purified viral structures, resuspended in PBS was first digested with DNaseI (5 U/50 µl supernatant) at 37° C. for one hour to remove any trace of contaminating free viral DNA. After DNaseI heat inactivation (10 min at 70° C.), purified viral structures were mixed (1:1 vol/vol) with lysis buffer (0.1 mg/ml proteinase K in water) and incubated for 60 min at 50° C., after which the enzyme was heat-inactivated (75° C. for 20 min). This step releases any viral DNA packaged into viral particles. Water diluted samples (1:10) were subjected to qPCR using primers and probe specific to the BALF5 DNA polymerase (pol) gene. Amplification reactions were performed in 25 µl volumes containing 12.5 µl Taqman Universal master mix (Applied Biosystems), 2.5 µl forward and reverse pol primers (2 µM), 1 µl 5 µM FAM-labeled pol probe, 1.5 µl water, and 5 µl purified and resuspended virus particles. Following activation of the AmpliTaq Gold DNA polymerase (10 min at 95° C.), the reaction mixtures were amplified for 40 cycles (15 s at 95° C., 60 s at 60° C.) and the fluorescent signals detected using an ABI 7300 Sequence Detection System (Applied Biosystems). The primer and probe sequences were as follows: reverse pol primer 5'-AGTCCTTCTTG-GCTAGTCTGTTGAC-3' (SEQ ID NO: 29), forward pol primer 5'-CTTTGGCGCGGATCCTC-3' (SEQ ID NO: 30), EBV pol probe 5'-FAM-CATCAAGAAGCTGCTGGCG-GCC-TAMRA-3' (SEQ ID NO: 31). The DNA content was calculated using a serial dilution of Namalwa DNA, a human Burkitt's lymphoma cell line that contains two EBV genome copies per cell, as a reference for the standard curve. The results of this assay are shown in FIG. 6; we found that gp350-purified viral structures from 1 ml wild type supernatants contains approximately 1×10E6 viral genomes. In medium and water controls the qPCR method gives a signal in the range of 1×10E3 to 1×10E4 genomes and therefore we draw a baseline at 1×10E4 genomes/ml. In stark contrast to wild type EBV, supernatants from induced 293/ΔBFLF1 and 293/ΔBBRF1 did not contain any detectable above the baseline EBV DNA. 293/ΔTR supernatants delivered intermediate results as one ml of supernatant contained slightly more than 1×10E4 viral genomes per ml of supernatants. Altogether we conclude that gp350-purified viral structures from induced 293/ΔBFLF1 and 293/ΔBBRF1 contain viral structures that carry the BNRF1 protein but do not contain any viral DNA, ie represent genuine VLPs.

Example 6

B Cells Pulsed with ΔBFLF1 and ΔBBRF1 VLPs are Recognized by EBV Specific T Cells We assessed the ability of VLPs to induce a T cell specific response (FIG. 7). To this aim, we incubated virus particles or VLPs present in 1 ml of the indicated virus supernatants purified using gp350 antibodies with LCL cells that acted as antigen-presenting cell. In parallel, LCLs were pre-treated with indicated amounts of BNRF1 peptide that were used as positive controls. The pulsed LCLs were then incubated with BNRF1-specific CD4+ T-cells. Specific recognition of antigens present at the surface of the LCLs by BNRF1-specific CD4+ T cells elicits production and release of IFN-gamma in the supernatant that can be assessed by ELISA. We found that the BNRF1-specific T cell recognize equally well wild type EBV virions and ΔBFLF1 and ΔBBRF1 VLPs.

Example 7

VLPs can Incorporate Foreign Proteins

Here we show that the intracytoplasmic and the transmembrane domains of the glycoprotein gC from herpes simplex virus can be used to introduce foreign antigens into VLPs. For example, we fused these sub-domains from gC in frame with 6 successive histidines (gC-6× his) and transfected a plasmid encoding this fusion protein into the ΔBFLF1 producer cell line upon initiation of the EBV lytic replication. Produced virus particles were purified using gp350 antibodies coupled to dynabeads. Proteins prepared from these VLPs were analysed by western blot using an histidine-specific antibody. We found that only viruses that were produced in 293/ΔBFLF1 cells transfected with the gC-6× his gave rise to specific signals and therefore have incorporated this protein (FIG. 8).

Example 8

VLPs Carrying Foreign Antigens Induce Immune Responses

Since we have shown that the LPs/VLPs we have generated are immunogenic and fulfil the requirements of a safe vaccine preparation, we aimed to enlarge their antigenic spectrum. EBV infection induces strong T cell responses and T cell epitopes from both EBV latent and lytic proteins have been identified. We chose the immunodominant epitope 5H11 (SEQ ID NO:33; coding sequence SEQ ID NO:32) from the EBV latent protein EBNA3C to be incorporated into the virus envelope. We generated a fusion protein (SEQ ID NO:35; coding sequence SEQ ID NO:34; the construct is comprised on plasmid B599 (SEQ ID NO:37); plasmid B557 (SEQ ID NO:36) is a control plasmid lacking the sequence encoding the 5H11 epitope), comprising the 5H11 epitope and parts of the glycoprotein C (gC) of Herpes Simplex virus 1 (HSV-1) including, the signal peptide, transmembrane domain and cytoplasmic tail. In addition, the construct contained a His tag and a unique restriction site to facilitate epitope insertion (FIG. 9A). Induction of mutant producer cell lines in the presence of this construct led to efficient incorporation of the fusion protein in EBV LPs/VLPs, as demonstrated by western blot of Dynabead-purified LPs/VLPs (FIG. 9B). Furthermore both ΔBFLF1/BFRF1A VLPs with incorporated gC-His-5H11 fusion protein were able to induce specific T-cell activation after presentation from LCLs (FIG. 9C).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09517261B2). An electronic copy of the "Sequence Listing" will also be available from the USPTO upon request and payment of the fee set forth in 37 CFR 1.19(b)(3).

The invention claimed is:

1. A preparation of Epstein-Barr virus-like particles (EB-VLPs) substantially free of Epstein-Barr Virus (EBV) DNA, wherein said EB-VLPs were generated from EBV lacking at least one functional gene selected from the group consisting of the BFLF1 gene, the BBRF1 gene, the BGRF1 gene, the BDRF1 gene, the BALF3 gene, and the BFRF1A gene; wherein, in the EB-VLPs substantially free of EBV DNA, the number of EBV DNA-free VLPs produced from said EBV lacking said at least one functional gene is increased as compared to VLPs produced from an EBV mutant strain in which the terminal repeats have been deleted (ΔTR-EBV).

2. The preparation of EB-VLPs of claim 1, wherein said EB-VLPs further comprise at least one artificial polypeptide.

3. The preparation of EB-VLPs of claim 1, wherein said EB-VLPs lack at least one additional non-essential EBV polypeptide.

4. A pharmaceutical composition comprising:
(a) a preparation of EB-VLPs according to claim 1, and
(b) at least one pharmaceutically acceptable carrier and/or excipient.

5. The pharmaceutical composition of claim 4, wherein the pharmaceutical composition is an immunogenic composition.

6. A polynucleotide comprising an Epstein-Barr virus (EBV) genome, wherein the polynucleotide is stably or transiently expressed in a suitable host cell, and wherein the polynucleotide:
(a) lacks at least one expressible gene selected from the group consisting of the BFLF1 gene, the BBRF1 gene, the BGRF1 gene, the BDRF1 gene, the BALF3 gene, and the BFRF1A gene, and
(b) is capable of producing the EB-VLP of claim 1.

7. The polynucleotide of claim 6, additionally lacking at least one expressible latent gene.

8. A vector comprising the polynucleotide of claim 6.

9. An isolated host cell comprising the polynucleotide of claim 6.

10. A method for manufacturing EB-VLPs substantially free of EBV DNA, comprising the steps of:
(a) culturing a suitable isolated host cell, wherein said cell comprises the polynucleotide of claim 6 or a vector comprising the polynucleotide of claim 6, and
(b) obtaining EB-VLPs substantially free of EBV DNA from the cells.

11. The method of claim 10, wherein said EB-VLPs are obtained from the supernatant of the cultured cells.

12. The method of claim 10, further comprising the step of expressing at least one gene coding for an artificial polypeptide in said host cell during step (a).

13. A method for the manufacture of a vaccine comprising the steps of the method of claim 10, and the further step of formulating the EB-VLPs as a vaccine.

14. A vaccine comprising EB-VLPs substantially free of EBV DNA obtainable by the method according to claim 13.

15. A composition comprising Epstein-Barr virus like particles (EB-VLPs) substantially free of EBV DNA obtained by the method according to claim 10.

16. The preparation of EB-VLPs of claim 1, wherein the number of EBV DNA containing VLPs is determined by infecting Raji cells and determining the number of Raji cells containing EBV DNA.

17. The preparation of EB-VLPs of claim 3, wherein said additional non-essential EBV polypeptide is the BNRF1 polypeptide.

* * * * *